United States Patent
Dash et al.

(10) Patent No.: US 6,846,664 B2
(45) Date of Patent: Jan. 25, 2005

(54) **PROCESS FOR THE PREPARATION OF PROTEASE INHIBITOR USING NOVEL ALKALOTHERMOPHILIC *BACILLUS* SP**

(75) Inventors: Chandravanu Dash, Maharashtra (IN); Sangita Uday Phadtare, Maharashtra (IN); Absar Ahmad, Maharashtra (IN); Vasanti Vishnu Deshpande, Maharashtra (IN); Mala Balchandra Rao, Maharashtra (IN)

(73) Assignee: Council for Scientific and Industrial Research, New Delhi (IN)

( * ) Notice: Subject to any disclaimer, the term of this patent is extended or adjusted under 35 U.S.C. 154(b) by 385 days.

(21) Appl. No.: 10/167,871

(22) Filed: Jun. 12, 2002

(65) Prior Publication Data

US 2002/0192797 A1 Dec. 19, 2002

Related U.S. Application Data

(62) Division of application No. 09/541,445, filed on Mar. 31, 2000, now Pat. No. 6,448,060.

(51) Int. Cl.$^7$ .............................. C12N 1/20; C12N 9/54
(52) U.S. Cl. .................... 435/221; 435/220; 435/252.5; 435/252.1
(58) Field of Search ................................ 435/220, 221, 435/252.1, 252.5

(56) References Cited

U.S. PATENT DOCUMENTS

| 5,358,865 A | 10/1994 | Outtrup | 435/221 |
| 5,385,837 A | 1/1995 | Boyer | 435/222 |

OTHER PUBLICATIONS

K. Horikoshi, Agr. Biol. Chem 35(9); 1407–1414, 1971.

*Primary Examiner*—Irene Marx
(74) *Attorney, Agent, or Firm*—John W. Renner; Renner, Otto, Boisselle & Sklar

(57) ABSTRACT

The present invention relates to a novel strain of alkalothermophilic *Bacillus* sp. isolated from a hot spring at Vajeshwari, District Thane, The State of Maharashtra, India and deposited at American Type Culture Centre (ATCC), bearing accession No. PTA 972, said strain of *Bacillus* sp. having the following characteristics (i) aerobic, (ii) gram positive, (iii) motile, (iv) spore forming, (v) capable of growing in a alkaline medium at pH 8–10, and (vi) exhibiting negative reaction towards production of indole, hydrogen, sulfide, ammonia and urease and positive reaction for hydrolysis of starch, production of catalase, hydrolysis of casein and reduction of nitrate.

6 Claims, No Drawings

PROCESS FOR THE PREPARATION OF PROTEASE INHIBITOR USING NOVEL ALKALOTHERMOPHILIC BACILLUS SP

This application is a divisional of U.S. application Ser. No. 09/541,445, filed on Mar. 31, 2000, now U.S. Pat. No. 6,448,060.

TECHNICAL FIELD

This invention relates to a novel strain of an alkalothermophilic *Bacillus* sp. More particularly the invention relates to a process for the preparation of a low molecular weight peptidic aspartic acid protease inhibitor using a novel strain of alkalothermophilic *Bacillus* (AT *Bacillus* sp.) deposited at American Type Culture Collection (ATCC) located at 10801 University Boulevard in Manassas, Va. 20110-2209, U.S.A., and bearing Accession Number PTA-972.

BACKGROUND OF THE INVENTION

Proteases are responsible either directly or indirectly for all bodily functions including cell growth, nutrition, differentiation and apoptosis. They also play a significant role in intracellular and extracellular protein turn over (house keeping and repair), cell migration and invasion, fertilization and implantation (Protease inhibitors, novel therapeutic application and development, Tony E Hugli, TIBTECH, 14, 409–412, 1996). Since proteases are necessary for normal and abnormal body functions, their effective regulatory counterparts i.e., protease inhibitors, are tremendously essential for physiological regulations. Protease inhibitors have been the source of attention in many disciplines. Due to their presence in valuable plant feeds and involvement in nutritive properties they have evoked the interest of nutritionists. Inhibitor proteins have been studied for the elucidation of mechanism of inhibition of proteases, as well as for the studies on protein-protein interactions and associations. Due to their unique pharmacological properties, protease inhibitors are also used as valuable tools in medical research.

Protease inhibitors are classified into Synthetic and Naturally occurring inhibitors. They occur in numerous animal tissues and fluids, in many plant tissues (particularly in legume seeds and other storage organs) and in microorganisms (Protease inhibitors, Yehudith Birk, Hydrolytic enzymes, A Neuberger and K. Brocklehurst (Eds), Elsevier Science Publishers B. V. (Biomedical Division), 257, 1987). The most abundant source of the inhibitors in plants is the seeds, but their location is not necessarily restricted to this part of the plant. They are also found in leaves, tubers, etc. As for the intracellular localization of the inhibitors, they appear to be associated primarily with the cytosol, but in some instances they have been localized in protein bodies. The inhibitors of animal origin are found both in tissues and in secretions of organs. The pancreatic trypsin inhibitor has been found as an intracellular component in various bovine organs: in the pancreas, lung, liver, spleen, paratoid gland and also in pituitary gland. In addition to the thoroughly studied pancreatic trypsin inhibitors, a large number of protease inhibitors from different animal sources have been isolated. Many of them are secretory proteins, such as trypsin inhibitors of blood plasma, milk colustrum, seminal plasma and submandibular glands. The plasma protease inhibitors constitute a major group of the functional proteins of the blood plasma. Most of them inhibit serine proteases but their mechanism of interaction is still being actively pursued by many investigators.

The presence of protease inhibitors in microorganisms came into existence from the studies on antibiotics as they act as inhibitors of the enzymes which are involved in growth and multiplication. Proteolytic enzymes outside of microbial cells hydrolyze organic nitrogen compounds in the medium, so they are thought to be harmful to cells. The production of inhibitors of the proteolytic enzymes by microorganisms is probably a mechanism to provide cell protection. In contrast to the inhibitors of proteolytic enzymes obtained from animals and plants, the inhibitors from microorganisms are of smaller molecular nature. Specific inhibitors of microbial origin have been used as useful tools in biochemical analysis of biological functions and diseases. (Enzyme inhibitors of microbial origin, Hamao Umezawa, University Park Press).

A few of the inhibitors of microbial origin of therapeutic interest are given below:

Leupeptin-from Streptomyces, is the inhibitor of trypsin, plasmin, kalikrein and papain.

Chymostatin-from Streptomyces, is the inhibitor of chymotrypsin.

Dopastin-from Pseudomonas, Oosponol-from Oospora, Oudenone-from *Oudemansialla radicata* and Fusaric acid-from Fusarium are the inhibitors of dopamine hydroxylase.

Pepstatin A-from Streptomyces, is the inhibitor of pepsin, an aspartic acid protease. It inhibits the HIV-1 protease, which is also an aspartic protease and the key enzyme for the propagation of the HIV.

The expanding Acquired Immuno Deficiency Syndrome (AIDS) epidemic and the relentless nature of the disease have intensified the search for effective antiviral therapies, to control the replication of the HIV, the causative agent of AIDS. The HIV-1 protease is the key enzyme for the propagation of the virus. Thus specific inhibition of the HIV-1 protease by inhibitors is useful in preventing the infection HIV-1 protease is structurally and mechanistically related to mammalian and microbial aspartic proteases such as pepsin, cathepsin, renin, and endothiopepsin. The classification of HIV-1 protease in the aspartyl family was also predicted from its primary sequence analysis. A highly conserved sequence Asp-Thr-Gly (D-T-G) in retroviral proteases, is also conserved in the active site of the cellular and fungal proteases. Molecular modeling studies have also confirmed the functional and structural similarities of the retroviral proteases to other aspartyl proteases. Various synthetic peptide and non-peptide compounds have been shown to inhibit HIV-1 protease. Well documented examples of isolation of compounds by microbial screening represented by the discovery of potent compounds such as cyclosprin, movionolin and avermycin, etc. An antifungal antibiotic cerulenin from Cephalosporium and pepstatin A, a pepsin inhibitor from Streptomyces, have been well characterized as HIV-1 protease inhibitors (C.Debouck, AIDS Research and Human Retroviruses, 8, 153–164, 1992).

Extensive evidence suggests that, the degradation of hemoglobin is necessary for the growth of erythrocytic malarial parasite, apparently to provide free amino acids for parasitic protein synthesis. On the basis of the data available, the aspartic acid proteases are thought to be responsible for the initial cleavages of hemoglobin. Both aspartic acid and cystein proteases have synergistic effects in inhibiting the growth of the cultural malarial parasite and also these proteases act synergistically to degrade hemoglobin. Therefore, the combination of inhibitors of malarial cystein and aspartic acid proteases, may provide a most effective chemotherapeutic regimen and best limit the development of parasitic resistant to protease inhibitors. Pepstatin, the inhibitor of aspartic acid proteases, along with the cystein protease inhibitor E-64, blocks the *Plasmodium falciparum* development. (Proteases of Malarial Parasite: New Targets for Chemotherapy, Philip J. Rosenthal, Emerging Infectious Diseases, 4(1), 49–57, 1998). So far no report is available for the preparation of the protease inhibitor using alkalothermophilic *Bacillus* sp.

Based on the fact that the aspartic acid protease plays a significant role in the development of the malarial parasite, the applicants believe that the inhibitor produced in accordance with the practice of the invention using the novel strain of *Bacillus* sp deposited at ATCC having Accession No. PTA 972, could be a potent inhibitor for proteases, particularly aspartic acid protease, and more particularly for proteases of malarial parasites. The inhibitor described in the present invention inhibits pepsin, an aspartic protease. Pepsin present in the gastric secretion is responsible for the degradation (digestion) of proteinaceous food. Excess secretion of pepsin has harmful effects on the stomach as it damages the digestive tract and causes stomach ulcer or duodenal ulcer. Considering the fact that the inhibitor is an active inhibitor of pepsin, it has potential application as a therapeutic agent against stomach or duodenal ulcers. Pepstatin A, a pepsin inhibitor has been reported to inhibit HIV-1 protease which is also an aspartic protease. The applicants have observed that the inhibitor also inhibits other enzymes having aspartic acid in the active site, and felt that the microbial protease inhibitor could inhibit HIV-1 protease.

OBJECTS

The main objective of the present invention is to provide a process for the preparation of low molecular weight peptidic aspartic acid protease inhibitor using a novel alkalothermophilic strain of *Bacillus* sp. deposited at American Type Culture Collection, and having Accession number PTA 972.

Another object of the invention is to develop an antifungal agent using the low molecular weight aspartic acid protease inhibitor developed in accordance with the process of the invention.

SUMMARY OF THE INVENTION

The invention provides a novel alkalothermophilic strain of *Bacillus* sp. deposited at ATCC and bearing Accession Number PTA 972. The invention also provides a process for the preparation of a low molecular weight aspartic acid protease inhibitor using the said novel strain and *Bacillus* sp.

DETAILED DESCRIPTION OF THE PREFERRED EMBODIMENTS

Accordingly, the present invention provides a process for the preparation of low molecular weight peptide aspartic acid protease inhibitor using an alkalothermophilic *Bacillus* sp. deposited at ATCC and having Accession Number PTA 972, said method comprising the steps of:

(i) subculturing the alkalothermophilic *Bacillus* sp bearing Accession Number PTA 972 in a fermentation medium at a temperature in the range of 37° C. to 50° C. under aseptic conditions for a period ranging between 24 to 48 hrs., (ii) harvesting the culture broth, (iii) separating the solids by conventional methods to obtain cell free liquid containing the protease inhibitor, (iv) treating the cell free liquid with a decolorising agent for a period ranging between 2 to 24 hrs to obtain a colorless liquid, (v) separating the decolorising agent and recovering the protease inhibitor by conventional methods.

The strain of alkalothermophilic *Bacillus* sp. employed in the present invention was isolated from the hot spring from Vajreshwari, District Thane, State of Maharashtra, India and has been deposited at the National Collection for Industrial Micro-organisms, NCL, Pune 411 008, India at Accession No. NCIM 59. The said strain of *Bacillus* sp. is also deposited at American Type Culture Collection and bears accession number PTA-972. The range of pH for the growth of the isolate was alkaline from 8–10 with an optimum growth at pH-10. No growth occurred below pH-7.0. The temperature range for the growth was 37–50° C. The strain was characterized as an aerobic, gram-positive, motile, spore-forming bacterium. On alkaline nutrient agar medium at 50° C., the colonies were butyrous, glistening and pale cream colored. The strain showed negative reaction towards production of indole, hydrogen sulfide, ammonia and urease, but positive reactions for the hydrolysis of starch, for the Voges-Proskuaer test, for the production of the catalase, for the hydrolysis of casein and for the reduction of nitrate. The organism produced oxidase, and ammonia was utilised as a nitrogen source. Acid but no gas was produced aerobically or anaerobically from D-glucose, D-mannose, D-fructose, and sucrose.

In an embodiment, the fermentation medium comprises assimilable carbon and nitrogen sources, malt extract, yeast extract, peptone, and micro-ingredients. The medium further comprises:

| | |
|---|---|
| 1. glucose | 0.5%–1% |
| 2. beef extract | 0.5%–0.75% |
| 3. sodium chloride | 0.1%–0.3% |
| 4. magnesium sulfate | 0.05%–0.1% |
| 5. dipotassium hydrogen phosphate | 0.05%–0.1% |
| 6. soyameal | 1%–2% |

In still another embodiment, assimilable carbon sources in the fermentation medium are selected from the group consisting of lactose, sorbitol, xylan, fructose, maltose and sucrose and the nitrogen sources are selected from the group consisting of soyameal, casein, casamino acids, urea, tryptone, beef extract, skimmed milk and yeast extract.

In a further embodiment, the protease inhibitor is recovered by treating the cell free supernatant with decolorizing agent, separating the low molecular weight compound from the supernatant by conventional methods selected from ultrafiltration, concentrating the filtrate by lyophilization, and purifying the inhibitor by reverse phase high performance liquid chromatography.

In an embodiment, the decolorizing agent, is selected from activated charcoal or cellulose.

In another embodiment, the production of the inhibitor and its activity is also dependent upon the nature and concentration of the media ingredients, inoculum development and parameters such as aeration, agitation, etc. In shake flasks maximum production was obtained after 24–48 hours, when a 5–20% v/v vegetative inoculum in the actively growing phase is transferred to the production media. Post fermentation processing of the broth for the isolation of the inhibitor includes, centrifugation or filtration of the broth. Cell free supernatant is treated with activated charcoal to remove the color material. The charcoal is removed by centrifugation or filtration. The resulting supernatant is subjected to ultrafiltration using filtration membranes.

In a feature of the invention, the pepsin inhibitor was selectively purified by removing the high molecular weight compounds from the culture broth by treating it with activated charcoal. The charcoal treated broth was filtered through ultrafiltration membrane and concentrated by lyophilization. The concentrated inhibitor sample was loaded onto a reverse phase-high performance liquid chromatography column using a linear gradient of acetonitrile and triflouroacetate, and the peaks were checked for the inhibitor activity. Among the two compounds detected in the HPLC analysis, the compound having less retention time showed the inhibition against pepsin. This compound absorbs strongly at 210 nm. The compound was collected and checked as a single purified peptide after loading onto the HPLC column. One unit of inhibitor is defined as the amount of inhibitor which inhibits the protease activity expressed in terms of decrease in optical density of 0.001 per minute.

Without being bound by any theory, the Applicants hereby state that the alkaline protease inhibitor developed in accordance with the process of the invention exhibits anti-fungal properties against a wide spectrum of fungi such as Aspergillus sp, Alternaria sp, Fusarium sp and Trichoderma sp., and is therefore useful as an anti-fungal agent.

The process of the present invention is described herein below with examples which are illustrative only and should not be construed to limit the scope of the present invention in any manner.

EXAMPLE 1

Eighteen hour grown AT *Bacillus* NCIM 59 on an agar slant, at 50° C., was inoculated into a medium containing glucose—1%, peptone—0.75%, beef extract—0.75%, sodium chloride—0.3%, dipotassium hydrogen phosphate—0.1%, magnesium sulfate—0.1% and soyameal—2.0%, and this fermentation medium was incubated on a rotary shaker at 50° C. for 12 hours 10% v/v of the freshly grown inoculum was added to the fermentation flasks. After 48 hours of growth on a rotary shaker at 50° C. the cells and the residual soyameal was removed by centrifugation. To 100 ml of centrifuged supernatant 10 grams of activated charcoal was added and incubated overnight at 4° C. This charcoal treated broth was filtered through filter paper 2–3 times to ensure there was no trace of charcoal remained. The maximum production of the inhibitor obtained was 100–112 U/ml in the charcoal treated broth.

EXAMPLE 2

The medium was formulated for the production flasks using lactose, sorbitol, xylan, fructose, maltose and sucrose, all at a concentration of 1% and fermentation process was carried out for 48 hrs. After 48 hrs. the production of inhibitor obtained was maximum of 98 U/ml in presence of sucrose.

EXAMPLE 3

In this example the fermentation medium used in example 1 was supplemented with amino acids for checking the effect on the production of the inhibitor. The amino acids used in the production flasks were alanine, arginine, asparagine, cystein, glutamic acid, glycine, histidine, proline and serine, all at a final concentration of 0.5%. After 48 hours, the product was isolated and the results are tabulated in Table 1 given herein below. It is observed that maximum production of the inhibitor of 105 U/ml was obtained in presence of asparagine.

TABLE 1

| Sl. No. | Name of the amino acid | Inhibitor Production In U/ml |
|---|---|---|
| 1. | Alanine | 55 |
| 2. | Arginine | 72 |
| 3. | Asparagine | 105 |
| 4. | Cystein | 36 |
| 5. | Histidine | 44 |
| 6. | Glutamic acid | 55 |
| 7. | Glycine | 61 |
| 8. | Proline | 8 |
| 9. | Serine | 16 |

EXAMPLE 4

The medium was formulated for the production of the inhibitor using 1% w/v of following nitrogen sources in the fermentation flasks. Soyameal, casein, casamino acids, urea, tryptone, peptone, beef extract, skimmed milk and yeast extract were among the nitrogen sources tested. Although, after 48 hours a maximum production of 70 U/ml of the inhibitor was obtained in presence of beef extract, the production was considerably high i.e., 90 U/ml–100 U/ml, when beef extract and soyameal were used together in the medium.

EXAMPLE 5

In this example the medium was supplemented with various inducers like soyameal, casein, yeast extract, tryptone, skimmed milk, urea and casamino acids, at a concentration of 1% w/v in the production flasks. After 48 hours, maximum production of 140 U/ml of the inhibitor was obtained in presence of casamino acids.

EXAMPLE 6

The charcoal treated supernatant was passed through an Amicon UM-10 and UM-02 membranes and concentrated by lyophilization. The activity of the inhibitor was also increased correspondingly. The concentrated inhibitor sample was injected into an RP-HPLC column in a linear gradient of 0–50% acetonitrile and 0.05% trifluoroacetate. The compound having less retention time, showed the inhibition against pepsin. This compound was recovered on RP-High performance liquid chromatography column using the same solvent system and found to be homogenous and pure. The purified inhibitor was analyzed for the amino acid sequences and for the determination of the molecular mass.

EXAMPLE 7

The fungal strains *Trichoderma reesei* (deposited at The National Collection for Industrial Micro-organisms, Pune India and bearing accession numbers NCIM 992, NCIM 1052- and NCIM 1186), *Fusarium oxysporum* (bearing accession numbers NCIM 1008, 1043, 1072), *Aspergillus flavus* (bearing accession numbers NCIM 535, 536, 538, 542), *Aspergillus oryzae* (bearing accession numbers NCIM 637, 643, 649, 1032), *Fusarium moniliforme* (bearing accession numbers NCIM 1099, 1100), *Alternaria alternata* (bearing accession numbers NCIM 887), *Claviceps purpurea* (bearing accession numbers NCIM 1046), *Curvularia fallax* (bearing accession numbers NCIM 714), *Curvularia lunata* (NCIM 716), *Curvularia cymbopogonis* (bearing accession numbers NCIM 695) and *Penicillium fellatanum* (bearing accession numbers NCIM 1227) were grown on potato dextrose agar slants for 7–8 days. The said fungal strains have characteristics similar to the strains deposited at American Type Culture Collection, USA and bearing accession number as under:

Trichoderma reesei NCIM 992-ATCC No.13631
Trichoderma reesei NCIM 1052-ATCC No.24449
Trichoderma reesei NCIM 1186-ATCC No.26921

Fungal mycelium from the freshly grown culture was inoculated at the centre of petri plates containing potato dextrose agar medium and incubated till they form small circular growth. The time period for the vegetative growth of different fungus is different. On the periphery of the advancing fungal mycelia, four filter paper discs were impregnated at equal distances, with four different concentrations of the inhibitor sample. The plates were incubated at room temperature for 24–48 h to check the crescent zone of the retarded mycelial growth. For sporulating fungus the applicants also had checked the inhibition by spore suspension method. In this method the agar slants were incubated at room temperature till they sporulate. 4 ml of sterile distilled water was added aseptically to the agar slant and the spores were scrapped by using an inoculation loop. 1 ml of this suspension was mixed with 4 ml of malt extract, glucose, yeast extract, peptone media containing 0.4% agarose and poured onto the potato dextrose agar plate. This plate was incubated at room temperature for 4–10 h. Filter paper discs were impregnated and different concentrations of the inhibitor was added onto it. The plates were further incubated at room temperature for 24–48 h and the inhibition zone against the growth was checked. The low molecular weight aspartic acid protease inhibitor was found to strongly inhibit the mycelial growth of *Aspergillus flavus* (NCIM 535, 542), *Aspergillus oryzae* (NCIM 637, 643), *Curvularia fallax* (NCIM 714), *Curvularia lunata* (NCIM 716), *Curvularia cymbopogonis* (NCIM 695), *Claviceps purpurea* (NCIM 1046), *Trichoderma reesei* (deposited at National Collection for Industrial Micro-organisms, Pune India and bearing accession numbers NCIM 992, NCIM 1052, NCIM 1186 respectively) having characteristics similar to the strains having ATCC accession Nos. 13631, 24449 and 26921 respectively, *Fusarium oxysporum* (deposited at National Collection for Industrial Micro-organisms, Pune India at accession numbers NCIM 1008, 1072 and having characteristics similar to the strains available at MI with accession No. 107510b) and *Alternaria alternata* deposited at National Collection for Industrial Micro-organisms, Pune India at accession No.NCIM 887 and having characteristics similar to the strain having ATCC accession No.11785.

The advantages of the Invention are

The bioactive microbial protease inhibitor reported in the present invention shows the inhibition against pepsin, an aspartic acid protease and other enzymes having aspartic acid in the active site. Hence, the inhibitor has potential to inactivate pepsin, HIV protease, as well as the aspartic acid protease of the malarial parasite. On the basis of the structure of the bioactive inhibitor as the lead compound, structurally related novel bioactive molecules can be designed. Protease inhibitors inhibit proteases that are common in animals and microorganisms. They are known to function as a natural phytochemical defense against predators, since they inhibit the proteases that occur in many species of herbivorous insects and plant pathogen. The low molecular weight protease inhibitor reported in this invention has antifungal property against phytopathogenic fungi. This is the first report of a low molecular peptidic aspartic acid protease inhibitor having antifungal property. So it can be used as an antifungal agent to control the fungal diseases of the plants. As a biomolecule it is biodegradable and does not have any hazardous effect on the environment.

Activity Details of the Inhibitor:

a) Assay of Pepsin Inhibition:

Pepsin inhibitory effect represented by the inhibitor was demonstrated by the following test.

The protease pepsin was incubated in KC1-HC1 buffer, 0.02 M, pH-2.0, containing the inhibitor in various molar ratios at 37° C. for 30 min. After incubation the residual activity was determined and compared with the controls incubated without the inhibitor.

For example—To 0.05 ml of 100 mg/ml of aqueous solution of pepsin, 0.1 ml of the inhibitor solution was added. The reaction was started by adding 1.0 ml of 0.6% casein aqueous solution (pH—2.0) and the mixture was allowed to stand at 37° C. for 30 minutes. 2 ml of 1.7 M aqueous solution of per-Chloric acid was added to stop the reaction. Precipitated excess casein was removed by filtration after incubation for one hour and the optical density was measured at 280 nm.

In comparison with the control test, the individual amount of the inhibitor required for a 50% inhibition of pepsin activity was determined, which is then represented by the term $IC_{50}$ as the measure of inhibitor thereof. The $IC_{50}$ value of the inhibitor obtained against pepsin in 25 mM.

b) Antifungal Activity Assay:

Inhibition of growth of fungi by the inhibitor was studied using inhibition assays against mycelial growth and spore germination.

For example-In case of mycelial growth inhibition assay, fungal mycelium from freshly grown culture was inoculated at the center of potato dextrose agar plate and incubated at 28° C. for 48–72 hours. Sterile filter paper discs impregnated with different concentrations of the inhibitor were placed on the periphery of the growing fungal mycelium. The plates were incubated at 28° C. and the crescent zones of the retarded mycelial growth were observed. In case of inhibition assay against spore-germination, fungal spore suspension was made in malt extract, glucose, yeast extract and peptone (MGYP) liquid medium. To the spore suspension, various concentration of the inhibitor was added. The resulting suspension was incubated at 28° C. for 24 hours. The germination of the spores in presence and absence of the inhibitor were checked under inverted microscope. The minimum inhibitory does MID of several fungal strains are given below in the Table 2.

TABLE 2

| SI. No. | Fungal Strain | MID (mg) |
|---|---|---|
| 1. | Aspergillus oryzae | 1.147 |
| 2. | Aspergillus flavus | 0.817 |
| 3. | Alternaria alternata | 0.582 |
| 4. | Fusarium oxysporum | 2.300 |
| 5. | Fusarium moniliforme | 1.840 |
| 6. | Trichoderma reesei | 0.292 |

What is claimed is:

1. A process for the preparation of low molecular weight peptidic aspartic acid protease inhibitor using alkalothermophilic *Bacillus* sp. deposited at ATCC at No. PTA-972, said process comprising the steps of:

i) growing the said strain of *Bacillus* sp. in a liquid fermentation medium containing assimilable carbon and nitrogen sources at a temperature in the range of 37–50° C. under aseptic conditions for a period of 24–48 hrs., ii) harvesting the culture broth, iii) separating the solids by conventional methods to obtain cell free liquid containing the protease inhibitor, iv) treating the cell free liquid with a decolourising agent, v) separating the decolourising agent and recovering the protease inhibitor by conventional methods.

2. The process as claimed in claim 1 wherein assimilable carbon sources in the fermentation medium are selected from the group consisting of lactose, sorbitol, xylan, fructose, maltose, and sucrose.

3. The process as claimed in claim 1 wherein the nitrogen sources are selected from the group consisting of soyameal, casein, casamino acids, urea, tryptone, beef extract, skimmed milk and yeast extract.

4. The process as claimed in claim 1, wherein the fermentation medium comprises:

| I. | glucose | 0.5%–1%, |
| II. | beef extract | 0.5%–0.75%, |
| III. | sodium chloride | 0.1%–0.3%, |
| IV. | magnesium sulfate | 0.05%–0.1%, |
| V. | dipotassium hydrogen phosphate | 0.05%–0.1%, and |
| VI. | soyameal | 1%–2%. |

5. The process as claimed in claim 1 wherein the protease inhibitor is separated from the supernatant by ultrafiltration, concentrating of the filtrate by lyophilization and purifying the inhibitor by reverse phase high performance liquid chromatography.

6. The process as claimed in claim 1 wherein the decolourising agent is selected from activated charcoal and cellulose.

* * * * *